United States Patent
Schmidt et al.

(10) Patent No.: US 10,123,531 B2
(45) Date of Patent: Nov. 13, 2018

(54) GRANULAR PLANT CONTROL COMPOSITION

(71) Applicant: Arch Chemicals, Inc., Atlanta, GA (US)

(72) Inventors: James Charles Schmidt, Colgate, WI (US); John Weber, Lilburn, GA (US); Ryan M. Wersal, Cumming, GA (US)

(73) Assignee: Arch Chemicals, Inc., Atlanta, GA (US)

(*) Notice: Subject to any disclaimer, the term of this patent is extended or adjusted under 35 U.S.C. 154(b) by 0 days.

(21) Appl. No.: 14/830,796

(22) Filed: Aug. 20, 2015

(65) Prior Publication Data

US 2016/0050912 A1 Feb. 25, 2016

Related U.S. Application Data

(60) Provisional application No. 62/039,680, filed on Aug. 20, 2014.

(51) Int. Cl.
*A01N 25/08* (2006.01)
*A01N 25/12* (2006.01)
*A01N 39/04* (2006.01)

(52) U.S. Cl.
CPC .......... *A01N 25/08* (2013.01); *A01N 25/12* (2013.01); *A01N 39/04* (2013.01)

(58) Field of Classification Search
None
See application file for complete search history.

(56) References Cited

U.S. PATENT DOCUMENTS

| | | | |
|---|---|---|---|
| 3,062,637 A | 11/1962 | Marples et al. | |
| 3,834,891 A | 9/1974 | Husted et al. | |
| 8,283,291 B2 * | 10/2012 | Yamaji | A01N 43/80 504/116.1 |
| 8,288,320 B2 | 10/2012 | Thompson et al. | |
| 2010/0260866 A1 * | 10/2010 | Lu | A01N 25/08 424/618 |
| 2012/0190547 A1 * | 7/2012 | Liu | A01N 43/653 504/136 |

FOREIGN PATENT DOCUMENTS

WO WO2007/139134 6/2007

OTHER PUBLICATIONS

Guggenheim et al., Clays and Clay Minerals 45: 255-256 (1995).*
Diatomaceous earth entry from Merriam-Webster On-line.*
Clay_Info—Continental Clay.*
Ng et al., "Experimental investigation of the silica gel-water adsorption isotherm characteristics", Applied Thermal Engineering 21: 1631-1642 (2001).*
Carfentrazone-ethyl entry—PubChem—open chemistry database.*
Merck Index—Diatomaceous Earth.*
OECD Guidance—2008.*
Agricultural Chemical Product Guideline—Feb. 2014 (Year: 2014).*
OECD Guidance—2008 (Year: 2008).*
PCT/US2015/045998 International Search Report and Written Opinion dated Oct. 1, 2015, 12 pages.
Guggenheim S. et al, Definition of clay and clay mineral: joint report of the AIPEA nomenclature and CMS nomenclature committees, Clays and Clay Minerals, Clay Minerals Society, US, vol. 43, No. 2, Jan. 1, 1995, pp. 255-256.

* cited by examiner

*Primary Examiner* — Thor Nielsen
(74) *Attorney, Agent, or Firm* — Dority & Manning, P.A.

(57) ABSTRACT

A plant or algae control composition is disclosed. The composition contains a herbicide and/or algaecide adsorbed onto a solid carrier. The composition may comprise a free-flowing granular product. The solid carrier contains a mixture of different clay materials. Two different clay materials are combined that synergistically mix together to allow for greater amounts of the herbicide or algaecide to be adsorbed onto the particles. The composition is particularly well suited for treating aquatic environments.

20 Claims, No Drawings

GRANULAR PLANT CONTROL COMPOSITION

RELATED APPLICATIONS

The present application is based on and claims priority to U.S. Provisional Patent application Ser. No. 62/039,680, filed on Aug. 20, 2014, which is incorporated herein by reference.

BACKGROUND

Many different pesticides, such as herbicides and algaecides, are commercially available for controlling unwanted plant and algae populations. The herbicides and algaecides are designed to limit growth and/or destroy a particular plant or algae or a broad range of plants and algae. The herbicide or algaecide may function in different ways. For instance, some herbicides and algaecides inhibit plant or algae growth by inhibiting photosynthesis. Other herbicides or algaecides are designed to be taken in by the plant or algae for inhibiting enzyme production. Other herbicides or algaecides may work as an oxidizer or may regulate plant growth by serving as an auxin mimic.

Of particular importance is that the herbicide or algaecide be capable of controlling growth or destroying a plant or algae population without harming the environment. For example, ideally a herbicide or algaecide will control plant or algae growth without having significant long-term adverse impacts on non-target organisms in the environment.

Particular problems are faced when attempting to control plant and algae growth in an aquatic environment, particularly in areas of high water exchange. Under these circumstances, the application of the herbicide or algaecide in controlled amounts can be difficult. Consequently, in some applications, the herbicide or algaecide is applied to a carrier in order to facilitate application of the herbicide or algaecide and to control the amount of herbicide or algaecide that is applied to the aquatic environment. The use of a carrier, however, can add cost to the product, especially in terms of shipping and handling. In addition, problems have been experienced in incorporating relatively high amounts of the herbicide or algaecide into the product, especially when solid carriers are used. For instance, some granular products may contain the algaecide or herbicide in amounts below 5% by weight. Consequently, relatively large amounts of the product need to be dispersed in the environment in order for the herbicide or algaecide to have sufficient efficacy.

In view of the above, a need exists for a plant control composition that includes a carrier for facilitating distribution or application of a herbicide or algaecide while being capable of containing relatively high concentrations of the herbicide or algaecide and thus minimizing the amount of carrier in the product.

SUMMARY

In general, the present disclosure is directed to a plant or algae control composition that is capable of controlling a plant or algae population. The plant or algae control composition is particularly well-suited for treating water bodies, such as lakes, rivers, ponds, streams, creeks, tributaries, canals, and the like. In accordance with the present disclosure, the plant or algae control composition contains a solid carrier. The carrier comprises a mixture or blend of clay materials. The carrier, for instance, includes a first particulate clay material combined with a second particulate clay material. The plant control composition further contains at least one herbicide or algaecide. The first clay material and the second clay material synergistically work together to increase the ability or capability of the composition to contain relatively high amounts of the herbicide or algaecide. For example, the herbicide or algaecide is adsorbed on the carrier in an amount greater than capable of being adsorbed onto an identical plant control composition that only contains the first clay material or onto an identical plant control composition that only contains the second clay material. In other words, by combining the first clay material with the second clay material, greater amounts of the herbicide or algaecide may be adsorbed onto the combined clay particles.

The resulting composition may be in granular form. As used herein, granular form includes small particle sizes such as powders and refers to a composition being comprised of particles and is to be distinguished from dispersions, suspensions, or gels. In one embodiment, the granular product can be free-flowing.

The amount of algaecide or herbicide contained in the composition can vary depending upon the particular herbicide or algaecide used and the type and amount of clay particles contained in the composition. In one embodiment, the plant control composition contains the herbicide or algaecide in an amount greater than about 10% by weight, such as in an amount greater than about 16% by weight, such as in an amount greater than about 18% by weight, such as in an amount greater than about 20% by weight, such as in an amount greater than about 21% by weight. The herbicide or algaecide is present in the composition generally in an amount up to about 55% by weight, such as in an amount up to about 50% by weight.

In one embodiment, the first clay material comprises a clay that forms a gel structure in water. In one embodiment, the first clay material may comprise attapulgite clay. The second clay material, in one embodiment, may be capable of absorbing water. For instance, the second clay material may be capable of absorbing at least about 60%, such as at least about 70%, such as at least about 80%, such as at least about 90%, such as at least about 100% of its weight in distilled water at 25° C. In one embodiment, the second clay material may comprise diatomaceous earth.

The first clay material and the second clay material may be present in the composition at a weight ratio of from about 1:9 to about 2.75:1 (e.g. the first clay material has a weight percentage of about 10 wt. % to about 73.33 wt. % of the total weight of the first and second clays, and the second clay material has a weight percentage of about 90 wt. % to about 26.6 wt. % of the total weight of the first and second clays), such as from about 1:4 to about 2.75:1 (first clay material ranges from about 20 wt % to about 73.3 wt %, and the second clay material ranges from about 80 wt % to about 26.6 wt %), such as from about 1:2 to about 1.5:1 (first clay material ranges from about 33.33 wt % to allow 60 wt %, second clay material ranges from about 66.66 wt % to about 40 wt %).

The herbicide or algaecide contained in the composition can vary. In one embodiment, the herbicide or algaecide may comprise dichlorophenoxyacetic acid or a derivative thereof. In one embodiment, the herbicide or algaecide is metal-free. For instance, in one embodiment, the herbicide or algaecide may be copper-free.

The present disclosure is also directed to a method of controlling a plant or algae population by contacting a plant or algae with the plant or algae control composition as described above. In one embodiment, the plant or algae is contacted with the plant or algae control composition by applying the composition to a body of water in which the plant or algae resides. When applied to a body of water, the herbicide or algaecide can be present in the water at a concentration of from about 0.001 ppm to about 50 ppm.

In other applications, the plant or algae control composition can be applied to plants in a field or on dry land.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to plant (including algae) control compositions for controlling a plant population. The composition generally comprises a herbicide and/or algaecide combined with a solid carrier. In accordance with the present disclosure, the solid carrier comprises a mixture of day particles. More particularly, the carrier includes a first particulate clay material combined with a second particulate day material. The herbicide and/or algaecide are adsorbed onto the day materials for producing a granular product.

According to the present disclosure, it was unexpectedly discovered that greater amounts of the herbicide or algaecide can be adsorbed onto the day mixture in comparison to the amount that may be adsorbed onto a similar composition containing only one of the clay materials. The first clay material and the second day material are synergistically combined together in a manner that allows the composition to adsorb a higher concentration of a liquid herbicide or pesticide than the concentration capable of being adsorbed onto the clays individually. In this manner, less of the solid carrier is dispersed into the environment when the environment is being treated with the herbicide or algaecide.

For example, in the past, many granular plant control products were only capable of adsorbing up to about 5% by weight of a herbicide or algaecide. The plant control composition of the present disclosure, on the other hand, can contain the herbicide or algaecide in an amount greater than about 10% by weight, such as in an amount greater than about 16% by weight, such as in an amount greater than about 18% by weight, such as in an amount greater than about 20% by weight, such as in an amount greater than about 21% by weight. In one embodiment, the plant control composition may contain the herbicide or algaecide in an amount greater than about 25% by weight, such as in an amount greater than about 30% by weight, such as in an amount greater than about 35% by weight. In general, the algaecide or herbicide is contained in the product in an amount less than about 60% by weight, such as in an amount less than about 55% by weight, such as in an amount less than about 50% by weight. The above amounts can be incorporated into the product while still maintaining the product in granular form. For instance, in one embodiment, the plant control composition can comprise a free-flowing granular product. In this manner, the carrier not only facilitates application of the herbicide or algaecide but also allows for relatively high concentrations to be incorporated into the product.

In general, any suitable herbicide or algaecide may be incorporated into the composition of the present disclosure. Herbicides and algaecides are generally categorized as systemic herbicides or algaecides or contact herbicides or algaecides. Systemic herbicides and algaecides have the capability to kill an entire plant and typically do so by being absorbed into the plant. Contact herbicides, on the other hand, cause parts of the plants to die that are in contact with the chemical.

In one embodiment, the herbicide or algaecide may be adsorbed onto the carrier in a liquid form. The herbicide or algaecide may also be water soluble. In one embodiment, a herbicide or algaecide is selected that is metal-free, and is particularly copper-free.

One example of a herbicide or algaecide that may be present in the composition of the present disclosure is 2,4-D. 2,4-D comprises dichlorophenoxyacetic acid. 2,4-D can be in liquid form that contains the dimethylamine salt of 2,4-D, or 2,4-D in the acid form, or any other form of 2,4-D. 2,4-D is a systemic herbicide that also has selectivity. 2,4-D is known to control Eurasian watermilfoil and other broad-leaved plants. 2,4-D serves as an auxin mimic and thus regulates plant growth.

Another example of a herbicide or aquacide is bispyribac-sodium. Bispyribac-sodium comprises sodium 2,6-bis[(4,6-dimethoxypyrimidin-2-yl)oxy]benzoate. Bispyribac-sodium inhibits the production of enzymes for controlling plant growth. For instance, bispyribac-sodium is known as an ALS inhibitor, meaning that the chemical inhibits acetolactate synthase.

Another example of an enzyme inhibitor that may be incorporated in the composition of the present disclosure is carfentrazone-ethyl. Carfentrazone-ethyl inhibits PPO enzyme and the production of chlorophyll. Carfentrazone-ethyl generally comprises Ethyl 2-chloro-3-[2-chloro-4-fluoro-5-[4-(difluoromethyl)-4,5-diydro-3-methyl-5-oxo-1H-1,2,4-trizol-1-yl)phenyl]propanoate.

In still another embodiment, the herbicide or algaecide may comprise a diquat. Diquat generally comprises 6,7-Dihydrodipyrido[1,2-a:2',1'-c]pyrazinediium dibromide. Diquat inhibits photosynthesis and thus can rapidly control target plants and some algae. Diquat is a relatively fast-acting non-selective herbicide or algaecide which controls plant foliage that it comes in contact with, but typically does not translocate to the roots.

Still another embodiment of a herbicide or algaecide that may be used in accordance with the present disclosure is endothall, which can comprise a liquid formulation. Endothall can comprise 3-dicarboxylic acid 7-oxabicyclo heptane-2. Endothall inhibits respiration and photosynthesis. Endothall is a non-selective herbicide or algaecide that works on contact and can work as a systemic pesticide. Endothall is typically used in very low concentration.

Another herbicide or algaecide that may be used is flumioxazin. Flumioxazin comprises a N-phenyl phthalimide and, similar, to carfentrazone-ethyl, inhibits PPO enzyme and chlorophyll production.

Fluridone may also be used as the herbicide or algaecide. Fluridone is a systemic herbicide or algaecide that may be used to control various aquatic plants, including Eurasian watermilfoil and other underwater plants. Fluridone is available as a liquid.

Another herbicide or algaecide that may be used is glyphosate. Glyphosate is a plant enzyme inhibitor and comprises N-(phosphonomethyl)glycine. Glyphosate may be used as a systemic broad spectrum herbicide to control floating-leaved plants like water lilies and shoreline plants like Purple Loose Strife.

In still another embodiment, the herbicide or algaecide may comprise imazamox. Imazamox comprises an ammonium salt of (2-[4,5-dihydro-4-methyl-4-(1-methylethyl)-5-oxo-1H-imidazol-2-yl]-5-(methoxymethl)-3-pyridinecarboxylic acid. Imazamox is a plant enzyme inhibitor and inhibits ALS.

Another embodiment of a herbicide or algaecide is imazapyr, which is also a plant enzyme inhibitor. Imazapry can inhibit ALS enzymes. Imazapry comprises (RS)-2-(4-Methyl-5-oxo-4-propan-2-yl-1H-imidazol-2-yl)pyridine-3-carboxylic acid.

Another embodiment of a plant enzyme inhibitor is penoxsulam. Penoxsulam can also inhibit ALS enzyme. Chemically, penoxsulam may comprise 2-(2,2-difluoroethoxy)-6-trifluoromethyl-N-(5,8-dimethoxy[1,2,4] triazolo[1,5,-c]pyrimidin-2-yl))benzenesulfonamide).

In still another embodiment, the herbicide or algaecide may comprise triclopyr. Triclopyr generally comprises a triethylamine salt, and particularly, (3,5,6-trichloro-2-pyridinyloxyacetic acid). Triclopyr is an auxin mimic similar to that of the aforementioned 2,4-D and therefore is a plant growth regulator. Triclopyr is relatively fast-acting and can serve as a systemic, selective herbicide. Triclopyr will control populations of Eurasian watermilfoil and other broad-leaved species such Purple Loose Strife. Of particular advantage, triclopyr can control Eurasian watermilfoil, Purple Loose Strife, and other plants without affecting many grasses and sedges.

In still another embodiment, the herbicide or algaecide may comprise an oxidizer. Examples of oxidizers include various peroxides, particularly activated peroxides. Examples of oxidizers include sodium carbonate peroxyhydrate and hydrogen peroxide and peroxyacetic acid. Oxidizers can provide immediate control of algae.

As indicated above, the herbicide and/or algaecide are combined with a solid carrier that comprises a mixture of clay materials. The solid carrier contains a first particulate clay material and a second particulate clay material that have been combined together. By combining the different clay materials together, greater amounts of the herbicide or algaecide can be adsorbed onto the carrier in comparison to using only one of the clay materials alone. Greater amounts of the herbicide or algaecide can be adsorbed onto the carrier while still producing a free-flowing granular product.

In one embodiment, the first clay material may comprise a clay that forms a gel structure in water. In another embodiment, the first clay material may comprise a calcined clay.

The first clay material, in one embodiment, may comprise an alumino-silicate clay, such as a crystalline hydrated magnesium alumino-silicate clay. For example, the first clay material may comprise attapulgite clay or sepiolite.

Attapulgite clays are a composite of smectite and palygorskite. The smectite component of attapulgite clays provides for an expanding lattice. The presence of palygorskite, on the other hand, can increase hardness. Attapulgite clays typically include palygorskite particles surrounded by a matrix of smectite.

In one embodiment, an attapulgite clay is incorporated into the composition that has been activated or calcined. Heat treating the clay, for instance, can increase the sorptive properties of the clay and increase hardness. Thermally activated attapulgite is well suited to adsorbing polar liquids.

Attapulgite clays are typically available with low volatile matter or regular volatile matter. The regular volatile matter grades typically have increased adsorptivity and break down more quickly in the environment.

The particle size of the first clay material can vary depending upon the particular application. Particle size can be measured using a mesh/sieve test. The mesh/sieve test measures how many of the particles pass through mesh openings of decreasing sizes in sequential sieves. In one embodiment, the first clay material or attapulgite clay may have a particle size distribution of 8/25 mesh. This means that almost all of the powder or particles pass through the 8 mesh (2.38 mm openings) and was trapped by the 25 mesh (0.707 mm openings). Consequently, greater than 50%, such as greater than 60%, such as greater than 70%, such as greater than about 80% of the particles have a particle size of from about 1 mm to about 2.2 mm.

The second clay material contained in the plant control composition, on the other hand, may comprise a clay that has excellent water absorption properties. For instance, in one embodiment, the second clay material may comprise a clay that is capable of absorbing at least 60%, such as at least 70%, such as at least 80%, such as at least 90%, such as at least 100% of its weight in water. In general, the clay material can absorb up to about 300% of its weight in water.

For instance, in one embodiment, the second clay material may comprise diatomaceous earth. Diatomaceous earth is a mineral composed primarily of the skeletal remains of microscopic aquatic plants, which are referred to as diatoms. Diatomaceous earth has relatively high absorption properties and has a low bulk density. Particles of diatomaceous earth can be hollow which makes the particles highly porous. Diatomaceous earth also has pesticide properties.

In one embodiment, diatomaceous earth may be used as the second clay material and may be activated by thermal treatment at temperatures greater than about 1200° F.

The diatomaceous earth particles can generally have a median particle size of from about 0.05 mm to about 0.5 mm. For instance, in one embodiment, the median particle size of the second clay material can be from about 0.1 mm to about 0.4 mm.

In one embodiment, the diatomaceous earth particles can have a particle size measured according to the mesh/sieve test such that greater than 95% of the particles pass through a 6 mesh screen (3.35 mm openings), while at least 99% of the remaining particles are trapped by an 80 mesh screen (180 micron openings). Consequently, at least 60%, such as at least 70%, such as at least 80%, such as at least 90% of the particles have a particle size of from about 200 microns to about 3.25 mm.

The first clay material and the second clay material are combined together in relative amounts that produce the desired synergistic effect. In particular, the clay materials are combined together in amounts such that the resulting mixture is capable of adsorbing greater amounts of a herbicide or pesticide than an identical composition that contains only one of the clay materials. In general, the plant control composition can contain the first clay material and the second clay material in a weight ratio of from about 1:9 to about 2.75:1 (e.g. the first clay material has a weight percentage of about 10 wt. % to about 73.33 wt. % of the total weight of the first and second clays, and the second clay material has a weight percentage of about 90 wt. % to about 26.6 wt. % of the total weight of the first and second clays), such as from about 1:4 to about 2.75:1 (first clay material ranges from about 20 wt % to about 73.3 wt % and the second clay material ranges from about 80 wt % to about 26.6 wt %), such as from about 1:2 to about 1.5:1 (first clay material ranges from about 33.33 wt % to about 60 wt %, second clay material ranges from about 66.66 wt % to about 40 wt %). The combined clay materials can be present in the plant control composition generally in an amount from about 30% to about 90% by weight.

In one particular embodiment, the plant control composition of the present disclosure contains attapulgite clay in an amount from about 20% to about 30% by weight, calcined diatomaceous earth in an amount from about 30% to about 40% by weight, and a herbicide or algaecide in an amount from about 20% to about 50% by weight. In one particular embodiment, the herbicide or algaecide may comprise dichlorophenoxyacetic acid or a derivative thereof.

The composition of the present disclosure can be used to treat all different types of plants and algae. The composition, for instance, may be used to control plant populations on land. Alternatively, the composition may be added to a water body for treating aquatic plants and algae. The water body may comprise a fresh water system, such as lakes, streams, creeks, reservoirs, water canals, ponds, and the like.

When treating water bodies, the composition can be added to an aqueous system such that the concentration of the herbicide or algaecide in the water is from about 0.001 ppm to about 50 ppm. The herbicide and/or algaecide concentration exposure time can vary depending upon various factors including the type plant or algae being treated, the type of herbicide or algaecide present in the composition, and water exchange characteristics of the site.

In an alternative embodiment, the plant control composition of the present disclosure may be used to treat dry land areas and fields. In this embodiment, the composition can be applied to land plants.

The plant control composition of the present disclosure may comprise a free-flowing granular product.

The present disclosure may be better understood with reference to the following example.

Example

The following procedure was carried out to demonstrate that a mixture of clays in accordance with the present disclosure can adsorb greater amounts of a herbicide in relation to the individual clays.

Three different clay samples were prepared. Each sample contained 60 grams of clay. Sample No. 1 comprised attapulgite clay only. Sample No. 2 comprised diatomaceous earth particles only. Sample No. 3 comprised a blend of the attapulgite clay and the diatomaceous earth. Sample No. 3 contained 43.5% by weight attapulgite clay and 56.5% by weight diatomaceous earth.

2,4-D herbicide was applied to each of the samples in incremental amounts until each sample contained the herbicide in an amount of 40% by weight (40 grams of herbicide). The following results were obtained.

After adding 32.9 grams of the herbicide, Sample No. 1 began to look wet and aggregated making the product unusable. At 36.2 grams of herbicide, the clay was completely saturated and unable to adsorb any more liquid.

Sample No. 2 began to clump, appear wet and physically break down after 34 grams of the liquid herbicide was applied. After 39 grams of the liquid herbicide were applied, the diatomaceous earth particles were completely saturated.

Sample No. 3 made in accordance with the present disclosure easily adsorbed all 40 grams of the liquid herbicide. Even after 40 grams of the liquid herbicide were applied to the blended clays, the material showed no clumping and did not appear wet. The individual clays remained intact. The resulting product was still in a free-flowing granular state.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A plant control composition comprising:
   a first particulate clay material, wherein the first clay material has a particle size such that at least 60% of the particles have a particle size of from about 0.8 mm to about 2.25 mm;
   a second particulate clay material mixed with the first clay material, the second clay material comprising diatomaceous earth, the second clay material being present in the composition at a weight percentage of at least 26.6% and up to 90% of the total weight of the first and second clay materials; and
   a herbicide or algaecide adsorbed onto the clay materials in an amount greater than capable of being adsorbed onto an identical plant control composition that only contains the first clay material or onto an identical plant control composition that only contains the second clay material, the resulting plant control composition being in free-flowing granular form, wherein the herbicide or algaecide is contained in the plant control composition in an amount greater than about 10% by weight.

2. A plant control composition as defined in claim 1, wherein the second clay material is present in the composition at a weight percentage of at least 26.6% and up to about 80% of the total weight of the first and second clay materials.

3. A plant control composition as defined in claim 1, wherein the first clay material comprises attapulgite clay.

4. A plant control composition as defined in claim 1, wherein the first clay material forms a gel structure in water.

5. A plant control composition as defined in claim 1, wherein the second clay material is capable of absorbing at least 60% of its weight in distilled water at 25° C.

6. A plant control composition as defined in claim 1, wherein the diatomaceous earth has been calcined.

7. A plant control composition as defined in claim 1, wherein the second clay material has a particle size such that at least 60% of the particles have a particle size of from about 200 microns to about 3.25 mm.

8. A plant control composition as defined in claim 1, wherein the herbicide or algaecide comprises dichlorophenoxyacetic acid or derivative thereof.

9. A plant control composition as defined in claim 1, wherein the herbicide or algaecide comprises a systemic herbicide or algaecide, the systemic herbicide or algaecide comprising dichlorophenoxyacetic acid or derivative thereof, bispyribac-sodium, carfentrazone-ethyl, a diquat, endothall, flumioxazin, fluridone, glyphosate, imazamox, imazapyr, penoxsulam, triclopyr, sodium carbonate peroxyhydrate, hydrogen peroxide and peroxyacetic acid, or mixtures thereof.

10. A plant control composition as defined in claim 1, wherein the herbicide or algaecide comprises a metal-free herbicide or algaecide.

11. A plant control composition as defined in claim 1, wherein the herbicide or algaecide is water soluble.

12. A plant control composition as defined in claim 1, wherein the plant control composition contains more than one herbicide or algaecide.

13. A method of controlling growth of a plant of algae population comprising contacting a plant or algae with the plant control composition defined in claim 1.

14. A method as defined in claim 13, wherein the plant or algae is contained in a body of water and the plant or algae is contacted with the plant control composition by adding the plant control composition to the body of water.

15. A method as defined in claim 14, wherein the plant control composition is added to the body of water such that the herbicide or algaecide is present in the water in an amount from about 0.001 ppm to about 50 ppm.

16. A plant control composition comprising:
a first particulate clay material;
a second particulate clay material mixed with the first clay material, the second clay material comprising diatomaceous earth, wherein the second clay material has a particle size such that at least 60% of the particles have a particle size of from about 200 microns to about 3.25 mm, the second clay material being present in the composition at a weight percentage of at least 26.6% and up to 90% of the total weight of the first and second clay materials; and
a herbicide or algaecide adsorbed onto the clay materials in an amount greater than capable of being adsorbed onto an identical plant control composition that only contains the first clay material or onto an identical plant control composition that only contains the second clay material, the resulting plant control composition being in free-flowing granular form, wherein the herbicide or algaecide is contained in the plant control composition in an amount greater than about 10% by weight.

17. A plant control composition as defined in claim 16, wherein the herbicide or algaecide comprises dichlorophenoxyacetic acid or derivative thereof.

18. A plant control composition as defined in claim 16, wherein the herbicide or algaecide comprises a systemic herbicide or algaecide, the systemic herbicide or algaecide comprising dichlorophenoxyacetic acid or derivative thereof, bispyribac-sodium, carfentrazone-ethyl, a diquat, endothall, flumioxazin, fluridone, glyphosate, imazamox, imazapyr, penoxsulam, triclopyr, sodium carbonate peroxyhydrate, hydrogen peroxide and peroxyacetic acid, or mixtures thereof.

19. A method of controlling growth of a plant of algae population comprising contacting a plant or algae with the plant control composition defined in claim 16.

20. A method as defined in claim 19, wherein the plant or algae is contained in a body of water and the plant or algae is contacted with the plant control composition by adding the plant control composition to the body of water.

* * * * *